(12) United States Patent
Prasch et al.

(10) Patent No.: US 6,596,318 B2
(45) Date of Patent: Jul. 22, 2003

(54) FIBRIN TISSUE ADHESIVE FORMULATION AND PROCESS FOR ITS PREPARATION

(75) Inventors: Armin Prasch, Freiburg (DE); Bernhard Luy, Freiburg (DE)

(73) Assignee: Glatt Process Technology GmbH, Binzen (DE)

( * ) Notice: Subject to any disclaimer, the term of this patent is extended or adjusted under 35 U.S.C. 154(b) by 0 days.

(21) Appl. No.: 09/845,682

(22) Filed: Apr. 26, 2001

(65) Prior Publication Data

US 2002/0037323 A1 Mar. 28, 2002

Related U.S. Application Data

(63) Continuation of application No. PCT/EP99/08128, filed on Oct. 27, 1999.

(30) Foreign Application Priority Data

Oct. 27, 1998 (DE) .......................... 198 49 589

(51) Int. Cl.⁷ ................................. A61K 9/50
(52) U.S. Cl. ................ 424/499; 424/489; 424/490; 424/530; 574/2; 574/21
(58) Field of Search ................ 424/530, 489, 424/490, 499; 514/2, 21

(56) References Cited

FOREIGN PATENT DOCUMENTS

| DE | 44 41 167 C1 | 11/1994 | |
| DE | 195 59 611 | 6/2000 | .......... A61K/38/36 |
| EP | 0 792 188 | 2/2000 | .............. B01J/2/16 |
| WO | WO96/29990 | 3/1996 | |
| WO | WO97/44015 | 11/1997 | |
| WO | WO99/15637 | 1/1999 | |

OTHER PUBLICATIONS

Article: by Prof. Dr. Rudolf Voight et al., "Lehrbuch der pharmazeutischen Technologie", 85 0570 EPO; Verlag chemie 1984.
Article: by D. Prunkard et al., XP–002112932 Sep. 6, 1997; "Heterologous production of recominant human fibrinogen, thrombin, and factor XII . . . " ZymoGenetics, Inc. and PPL Therapeutics.
Article: by Torben Schuefer et al., "Control of fluidized bed granulation v. Factors affecting granule growth", Arch. Pharm. Chemi, Sci. Ed. 6. 1978. 69–82. Rec'd. Nov. 8, 1977.

*Primary Examiner*—Jean C. Witz

(57) ABSTRACT

A solid formulation of a fibrin tissue adhesive for use in medical procedures is disclosed. The formulation is a mixture containing thrombin and fibrinogen with factor XIII in a pourable solid granule form. The granules are obtained by drying the protein solutions or suspensions in a fluidized bed apparatus. Preferably, the granules have a particle size between 20 and 1,000 um.

19 Claims, 2 Drawing Sheets

FIBRIN TISSUE ADHESIVE FORMULATION AND PROCESS FOR ITS PREPARATION

Figure 1:
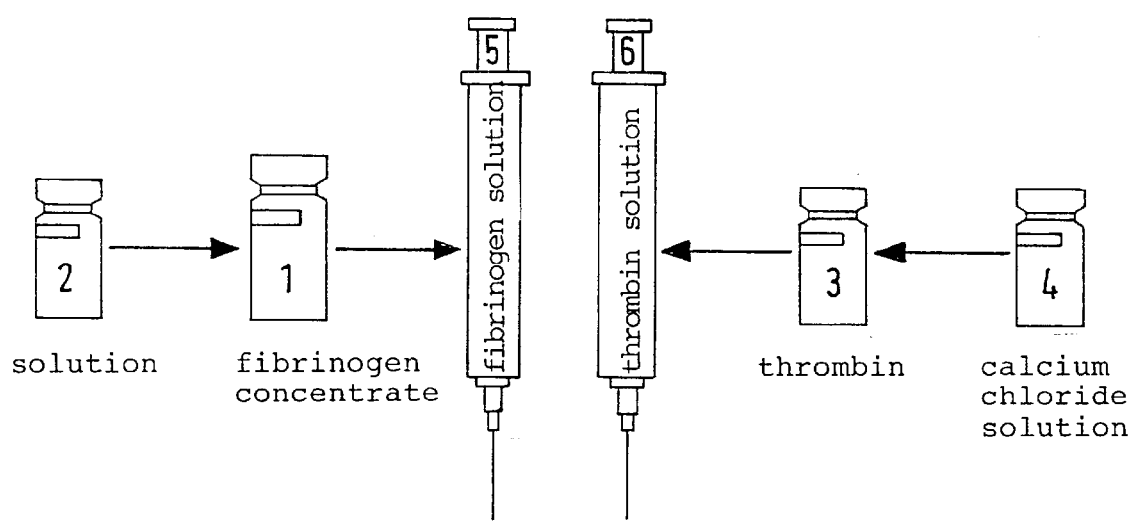

This is continuation of application Ser. No. PCT/EP 99/08128 filed Oct. 27, 1999.

FIELD OF THE INVENTION

The invention relates to a suitable formulation of a stable, pulverulent, as free from dust as possible and hence very pourable, solid administration form of a fibrin tissue adhesive for use in haemostasis, wound care (wound healing), tissue adhesive and securing sutures for external and internal surgical operations on humans, wherein the formulation can be prepared by means of a fluidised bed or spray-drying process or by a suitable combination of both drying processes.

BACKGROUND OF THE INVENTION

Blood clotting in the healthy body of animals (mammals) and in the human being proceeds naturally in the form of a co-enzyme/enzyme controlled cascade reaction. The main step consists in the soluble (in water, physiological saline solution and also in blood) fibrinogen being converted to the insoluble fibrin. The proteolytic enzyme thrombin is necessary for this and is formed by the prothrombin activator, a mixture of Stuart Prower factor (factor X) and proaccelerin (factor V) in the presence of calcium ions from the inactive prothrombin (factor II). The thrombin cleaves the fibrinogen usually present as monomer (75%) having a molar mass of 340,000 Dalton, as dimer (15%) and as polymer (10%) into fibrin and thus forms long molecular chains. The latter are linked by the fibrin-stabilising factor XIII (and in the presence of calcium ions) to form a stable, cross-linking fibrin polymer. The smooth interplay of a series of factors (clotting factors) is necessary for this biochemical reaction. In the healthy organism the clotting factors required are present in adequate quantity in a labile equilibrium.

Disturbances to this equilibrium may be a danger to life. Disturbances of the equilibrium may be caused, apart from the hereditary lack of a clotting factor (for example haemophilia), during severe tissue bleeding, for large surface area, diffuse bleeds (soft tissue bleeds), which cannot be stopped by mechanical closure of arterial or venous vessels, or by therapeutically administered medicaments acting as an anti-coagulant for the prophylaxis of thromboembolism. These disturbances may be compensated by so-called fibrin tissue adhesives, a mixture of fibrinogen, factor MII, thrombin and human albumen as well as calcium chloride, resulting in local homeostasis. Fibrin tissue adhesives are therefore used in many different applications.

For surgical interventions on tumors, particularly in mouth-jaw-face surgery as well as the overall ENT field (for example tongue carcinoma resection) there are often diffuse bleeds which are difficult to control. Electrosurgical homeostasis by electrocoagulation which is often used conventionally leaves behind extensive thermal tissue scars after coagulation, which are extremely undesirable, particularly in these areas.

In plastic-aesthetic face and neck surgery ("face-lifting"), homeostasis using fibrin adhesive is indispensable, since electrocoagulation is a danger to the facial nerve because of the anatomical proximity of the treatment site to the path of the facial nerve and may damage the latter.

Furthermore, treatment with a fibrin tissue adhesive is indicated for non-stopping bleeds in emergency treatment for dental surgical interventions. This also applies to patients who are treated with anti-coagulant medicaments because of a certain underlying disease (for example treatment for prophylaxis of embolism with heparins) and have to be operated on in spite of the associated risk of inhibited blood clotting (extended blood clotting, inhibition of thrombocyte function). In this case measures which guarantee homeostasis and avoid post-operative bleeds, should therefore be taken by means of local application of a fibrin tissue adhesive. This may become necessary, for example even for operations on internal organs (for example liver, spleen). The tissue adhesive may thus be supplied externally by endoscope via a double catheter.

Furthermore, the use of a fibrin tissue adhesive is indicated in emergency care of large surface area wounds due to third degree burns as well as large surface area excoriation.

When administering and applying a fibrin tissue adhesive, care should be taken to ensure that fibrinogen and thrombin are only brought together directly at the site of the bleed (that is "in the wound"), since the onsetting clotting starts spontaneously in the presence of wound fluid. Neighbouring sites should thus be well covered. A precondition for clotting is the freedom to move of the individual participating molecules, for example in water. In practice this is realised in that, for example the four different components (fibrinogen-factor XIII concentrate, solution for fibrinogen, thrombin concentrate, calcium chloride solution for thrombin) are stored separately before application and are only brought into mutual contact directly at the wound. The components must be packed in sterile manner in each case and be stored in a suitable form and under defined conditions, so that the activity of the individual proteins or enzymes is not damaged by storage. This is usually achieved so that the protein concentrates are present in freeze-dried form in small containers. They are stable to storage in this form under refrigerator conditions (4 to 8° C.) for a certain time and for a shorter time even at room temperatures (20° C.). However, freeze-dried the concentrate is present in solid, compressed and thus immobile form, but as a soluble solid. Therefore the protein concentrates must be completely dissolved again before application in order to be able to start the required biochemical reaction (FIG. 1). However, this may only be effected directly at the wound, so that each of the solutions has to be prepared separately from the other beforehand. Before application of the fibrin tissue adhesive the wound should then be as dry as possible, which in some cases can only be achieved with difficulty for large surface area, diffuse bleeding in order to facilitate good fixing of the tissue adhesive there and then. The two solutions may be added in each case via injection syringes, for example in the same volume ratio. Hence the fibrinogen solution should be applied initially to the wound and coated as soon as possible with the thrombin solution. The parts to be adhered should then be fixed until provisional solidification has taken place. Alternatively, there are mechanical aids, for example in the form of a double-chamber injection syringe, by means of which both solutions may be applied to the wound at the same time. Further technical auxiliaries are, for example spray tip systems for large surface area wounds, double-balloon catheters in urology or double catheters for endoscopic application. The concentration of the proteins in both solutions must be adjusted so that fibrinogen is present in significant excess with respect to thrombin. Suitable ratios are known according to the state of the art (for example 100:1).

This makes it clear that application requires on the one hand a qualified and concentrated preparation, which cannot always be ensured in some emergency situations. On the other hand application by the clumsy and manual handling of the 2-syringe system is likewise restricted.

A spray-dried tissue adhesive formulation is known from World application 97/44015. However, these microparticles have a defined size distribution up to 50 μm in diameter, reproducibly with 90% or more up to 20 μm in size. Hence this product is not pourable and is difficult to meter. It has been shown that this product not only forms dust when it is applied but also has poor solubility.

THE OBJECT OF THE INVENTION

The object of the present invention is therefore to indicate a fibrin tissue adhesive formulation which is simple to handle, meter and apply and can be stored without problems over a longer period, so that the possibilities for use of such a fibrin tissue adhesive formulation are significantly expanded with respect to the state of the art.

The object of the invention is likewise to indicate a corresponding process for producing such a fibrin tissue adhesive formulation.

The object is achieved with regard to the formulation by the characterising features of claim 1 and with regard to the process by the characterising features of patent claim 15.

The sub-claims show advantageous further developments.

SUMMARY OF THE INVENTION

It is thus proposed according to the invention that the fibrin tissue adhesive formulation is present in solid pourable form as a mixture of the different protein concentrates, wherein the granule size lies in the range between 20 and 1,000 μm and hence handling and application are problem-free. It is thus essential to the invention that the granules present in the formulation are produced by drying of the protein solution in a fluidised bed, since it has been shown, surprisingly, that such gentle drying of the protein solutions or suspensions is possible using this process that their functional properties do not change.

A further advantage can be seen in that the granules are present in pourable form so that exact metering is possible.

The fibrin tissue adhesive formulation according to the invention thus has far-reaching advantages with respect to the state of the art. The invention is characterised in particular in that the mixture (=the fibrin tissue adhesive) does not react (that is trigger clotting) as long as it is present in this solid form;

the mixture (=the fibrin tissue adhesive) is present in solid and yet at the same time pulverulent or granular, hence pourable and dust-free form resulting in it being possible to apply the mixture directly to the would to be tended without the protein components (fibrinogen-factor XIII concentrate and thrombin concentrate) having to be dissolved before application;

the mixture (=the fibrin tissue adhesive) is dissolved well, completely and quickly in the wound fluid;

the mixture (=the fibrin tissue adhesive), after is has dissolved or while it is dissolving in the wound fluid, triggers the biochemical reaction of blood clotting and forms a self-fixing solid layer and hence represents good wound care;

due to the possibility of being able to vary the particle size comparatively simply, new application possibilities result. By way of example in the form that it is possible either to be able to strictly localise wound contact by varying the particle size during metering (for homogeneously distributed, larger particles) or to also facilitate large surface area contact in a thin powder layer (for example by spray systems for fine granules);

different mixing ratios of both components mixed as a granule mixture can be easily adjusted and hence the properties of the fibrin tissue adhesive (solubility, onset of clotting) may be adjusted specifically;

due to the fact that powder can be mixed very homogeneously, the "content uniformity" can be ensured with certainty, even if a broad particle size spectrum exists (that is that the required mixing ratio always exists independently of particle properties, such as grain size density, and others).

The fibrin tissue adhesive formulation of the invention preferably also contains a calcium salt, for example $CaCl_2$ and may thus be composed so that either the individual protein solutions or suspensions, that is the fibrinogen-factor XIII solution or suspension and the thrombin/$CaCl_2$ solution or suspension are dried separately and then the dried granules are mixed, or that during drying of the protein solution the fibrinogen is initially dried and then the thrombin is applied to these granules thus produced. A structure is also possible in which the thrombin forms the core.

For the fibrin tissue adhesive formulation according to the invention it should also be emphasised that it may be adjusted depending on application. Hence, in the tissue adhesive formulation firstly the mixing ratio of fibrinogen to thrombin may be selected specifically depending on application, secondly control of the particle size is also possible.

For the fibrin tissue adhesive formulation in which in each case separate granules of the particular proteins are produced initially and are then mixed, it is also possible that the granules consist of a core, of an carrier material and a protein layer applied thereto. The carrier material may consist, for example of water-soluble sugars and/or sugar substitutes and/or biological transport substances. Examples are mannitol or serum albumen.

The formulation is preferably produced so that the particle size of the granules lies in the range from 30–500 μm, preferably 40–200 μm.

Fibrin tissue adhesive formulations having a core, that is having a carrier material, are also preferred for the mixed granules. In this case the granules then consist of a core, for example again of mannitol, to which a fibrinogen layer is then applied, over which the thrombin layer is then arranged. Accordingly, these mixed granules have a three-layered structure. Of course it is also possible according to the present invention that these mixed granules are produced with a core. In the embodiment with the mixed granules it is also preferable if a barrier layer is arranged between the fibrinogen layer and the thrombin layer. This barrier layer must firstly separate the fibrinogen layer from the thrombin layer and must secondly also be very water-soluble. Materials for this barrier layer must therefore fulfil the two above-mentioned criteria. Examples of them are low-molecular polyvinylpyrrolidones or also cellulose derivatives or also carbohydrates, for example dextrose derivatives.

The invention also relates to a process for producing the fibrin tissue adhesive formulation described above.

It is proposed according to the invention that the proteins occurring typically in the fibrin tissue adhesive fibrinogen, thrombin, factor XIII and calcium salt be dried gently in a fluidised bed apparatus, so that a pourable, granular solid is thus produced. A suitable device for this is described in German 4 441 167. Reference is therefore made to this disclosure content.

The process is preferably executed so that the fluidisation gas is passed through the fluidised bed chamber from bottom to top and the liquid (solution or suspension) to be dried is sprayed in from the top (top spray), from the bottom (bottom spray) or also laterally (rotor fluidised bed) via a spraying system. The fluidisation gas has at the same time the task of fluidising product present in the fluidised chamber, supplying the necessary heat for evaporating the spray liquid (water or organic solvent) to the spray jet or the moist product, and at the same time taking up the evaporated quantity of liquid and transporting it away. Discharge of the dried product is prevented on the one hand by selecting a suitable fluidisation rate (less than the so-called discharge rate for the product which can be determined by calculation and experimentally), on the other hand also by a product restraining filter present in the upper region of the fluidised chamber and which can be cleaned regularly, or also by a further product separator known from the state of the art (such as for example a cyclone separator).

It is thus possible to proceed, for example such that the carrier material is placed in the fluidised chamber, onto which the solution/suspension is then sprayed, for example from aqueous protein solution or suspension. The liquid droplets finely atomised in the spraying cone thus meet the fluidised pulverulent carrier material and dry there due to the heat and mass transfer conditions which are ideal for fluidised bed processes and are essentially a result of the very large specific particle surface area of the fluidised product. The proteins present in the spray liquid are then deposited on the carrier as solid due to adsorptive forces. The carrier is ideally provided so that on the one hand it is inert with respect to the proteins (that is there can be no interaction with the protein structures, which would change the functional properties permanently) and that at the same time the solubility of the proteins in water, wound fluid or physiological saline solution is restricted or prevented. Therefore suitable substances are, for example sugars (for example mannitol) which have good solubility in water, or also other substances known according to the state of the art as carrier materials which have good solubility in water. However, they must, due to the very specific properties of the proteins, be evaluated individually for their suitability. Substances which already function as transport systems in the biological system and which may therefore be used at the same time, are also suitable as carriers, since they are present in the natural, biological systems in addition to the required proteins of the fibrin tissue adhesive. Serum albumen of human origin or in recombinant form may be mentioned as an example of this.

During spraying, agglomerates or granules are formed due to the product moisture slowly increasing in the particle and hence there is an increase in particle size. In order to obtain good water solubility, it may be advantageous to produce amorphous granule structures having the large specific surface areas resulting therefrom. Suitable process conditions (variation of the spraying pressure, spraying rate, product temperature and feed air temperature, solid concentration of the spraying solution used), for producing these structures in defined manner and reproducibly, are known according to the state of the art of fluidised bed processes. By adding water-soluble binders known according to the state of the art (for example cellulose derivatives), it is possible to vary the particle size with respect to size and grain size distribution (Schäfer, T.; Worts, O.; Control of fluidized bed granulation. V. Factors affecting granule growth. Arch. Pharm. Chemie. Sci. Ed. 6, 1978, 69–82).

Using exact adjustment of a certain particle size, the requirements “pourability” (and hence also meterability), “solubility”, “freedom from dust” and “mixability” may be adjusted satisfactorily and also varied specifically. Hence it is advantageous to facilitate a large surface area, finely dispersed application of the fibrin tissue adhesive with as fine and small as possible a particle size. At the same time due to larger particles with narrower particle size distribution, a locally severely limited, specific metering of the fibrin tissue adhesive may become possible. For example the solubility of the granules may be a further degree of freedom for application of a solid, pourable fibrin tissue adhesive. Hence, for example maximum rapid solubility or a delayed solubility and thus also delayed or slower onsetting clotting may be adjusted. This slow or delayed clotting may provide additional possibilities for additional manipulation or change in operative interventions, for example in plastic-aesthetic face operations. The solubility can be influenced both via the particle size, the particle structure and via additional substances which increase or lower the internal binding forces.

When selecting the process conditions, care must primarily also be taken to ensure that the relevant proteins are not damaged (for example by high temperatures). Suitable feed air temperatures lie, for example between 15 and 100° C.; however, for the product temperature less than 50 or 37° C. is preferred. It must be taken into account in the process that possible inactivation must always be considered in connection with a certain moisture, that is the heat stability increases with decreasing product moisture in the solid, so that higher temperatures may also be acceptable towards the end of drying.

Drying must take place to residual moisture which is so small that no activity losses are observed, depending on the selected storage conditions, or that clotting already proceeds automatically. Suitable storage conditions are: cool storage at 4 to 8° C. or room temperatures (20° C.). The granules may additionally be enclosed in a protective atmosphere (for example nitrogen or carbon dioxide) and, for example with exclusion of light. Possible residual moistures may then lie, for example between 0.1–5% water content.

BRIEF DESCRIPTION OF THE DRAWINGS

The invention is illustrated in more detail below by examples and FIGS. 1 and 2.

FIG. 1 shows schematically the 2-syringe model,

FIG. 2 shows a fluidised bed plant for carrying out the process.

DETAILED DESCRIPTION OF THE INVENTION

General guidelines for producing the granules:

(1) The fibrinogen concentrate (together with the factor XIII) is sprayed onto provided mannitol (having particle size 50–100 μm) from aqueous solution. The ratio of carrier material to quantity of protein may be varied, for example in a range from 1:1 to 100:1 and preferably lies in a range from 1:1 to 10:1. Drying is carried out to the suitable residual moisture, the product temperature does not exceed the temperature of 35° C. during spraying and subsequent after-drying.

(2) The thrombin concentrate is then sprayed in the same manner onto likewise provided mannitol (having particle size 50–100 μm) from aqueous solution having a defined quantity of calcium chloride. Since thrombin has the significantly lower portion in terms of quantity in the fibrin tissue adhesive, the ratio of carrier material to protein quantity for thrombin lies, for example in a range from 50:1 to 1,000:1 and preferably in the range 50:1 to 200:1. Following spraying, drying likewise takes place to a suitable residual moisture while maintaining maximum product temperature of 35° C. Both granules obtained are then mixed and may then be applied directly to the wound as a mixture. The mixing ratio depends on the ratio of fibrinogen to thrombin preset according to the state of the art, as is also set for the hitherto known liquid forms of administration. Furthermore, other mixing ratios of fibrinogen granules to thrombin granules can however also be adjusted satisfactorily and easily (in contrast to solutions where the volume ratio has to be matched to the solubility).

Hence the effect of the fibrin tissue adhesive as regards onset on clotting, start of irreparable solidification or even solidity of the completely clotted adhesive, may be influenced easily and specifically by defined, homogeneous mixtures.

Alternatively, a fibrin tissue adhesive may also be produced according to the following process cycle:

(3) Carrying out drying of fibrinogen as described under (1) (on carrier material).

(4) Thrombin is sprayed onto the dried granules from an organic suspension (for example isopropanol is suitable) together with calcium chloride. Thrombin (and also fibrinogen) is stable in isopropanol, is not chemically changed in the process, but cannot be dissolved in isopropanol. Thrombin is thus deposited on the granules charged with fibrinogen. As a result of the absence of water there is no premature clotting, for example even on the granules during spray granulation. The mixed granules consisting of carrier, fibrinogen-factor XIII and thrombin may be applied directly to the wound. Proportions of fibrinogen to thrombin again correspond to the ratio known from the state of the art. The solubility, and associated therewith also clotting, is increased in these mixed granules, particularly also by the absence of a considerable quantity of carrier material which does not have to be dissolved first for application.

(5) In order to facilitate direct spraying of thrombin-containing, aqueous solution (+$CaCl_2$ on provided fibrinogen granules (produced according to (1)), for example an easily water-soluble barrier layer may be applied to the fibrinogen granules as an inner barrier for spatial separation of fibrinogen and thrombin. For this barrier layer the following applies: that firstly both active ingredients may not be chemically changed in the process, that the barrier layer is easily dissolved in water and that it is an effective separation of fibrinogen and thrombin during spraying and granulation and also in the final, storage-stable, solid, dried form. Low-molecular polyvinylpyrrolidone or also cellulose derivative solutions or also carbohydrates (for example dextrose derivatives) are suitable examples of this. The same characteristics as regards solubility and cloning can be expected for the product thus produced as for the granules produced according to (4).

In addition, process variants without an additionally provided carrier material are also possible:

(6) Granule seeds or finely divided particles, which may serve as starter cores for further granulation, are produced in situ by spraying from aqueous fibrinogen solution or from isopropanolic (or organic) suspension into an empty plant. The plant used for this may be, for example a spraying tower or also a fluidised bed plant having adequate free flue path for the sprayed liquid droplets. By adhering to suitable process conditions, the sprayed liquid droplets may be dried in a fluidised bed plant in accordance with the conditions of a spray drier (but at reduced drying temperatures), before they contact the container wall, for example in the still moist state, and remain stuck there. These fine particles thus produced are set in motion by the fluidisation gas and kept suspended and thus come into contact with the spray cloud of the further sprayed liquid and then start to form granules. Defined granule growth may be generated in this manner, particularly by very careful operation of the process during start-up of the process, in the originally empty plant. Growth may be assisted, for example by adding known binders. By combining with classifying granule discharge (for example via a zigzag sifter and classifying air stream) there is the possibility of producing granules having a defined particle size in the plant and even operating the process in a continuous or quasi-continuous manner.

(7) Thrombin with or without an additional barrier (or coating) layer may be applied directly as described under (4) or (5) to the fibrinogen concentrate granules produced according to (6).

According to the state of the art, the production variants (1)–(7) for the fibrinogen tissue adhesive may or must be combined with suitable processes for inactivation of viruses. This may be effected either so that the protein concentrates are treated before drying using known inactivation processes (for example pasteurization or solvent/detergent processes), or that the dried granules, as known from German 4 441 167, are heat-treated directly in the fluidised bed towards the end or after the actual spray granulation or drying such that the viruses are accordingly inactivated. However, this treatment step must be carried out so that the functional properties of the proteins are retained.

FIG. 1 shows the schematic representation of the necessary preparation of the different components of a fibrin tissue adhesive before application and possibilities for administration according to the state of the art.

1 Fibrinogen-factor XIII concentrate
2 Solution (for example physiological saline solution)
3 Thrombin concentrate
4 Calcium chloride solution Components 1–4 have sterile packaging. The solutions of components 2 and 4 are usually introduced into bottles 1 and 3 by means of vacuum. After a complete solution (without clouding) has formed in containers 1 and 3, the solution may be drawn into sterile syringes (5) and (6) and administered onto or into a wound. The quantities used lie typically in the ml range.

Figure 2:
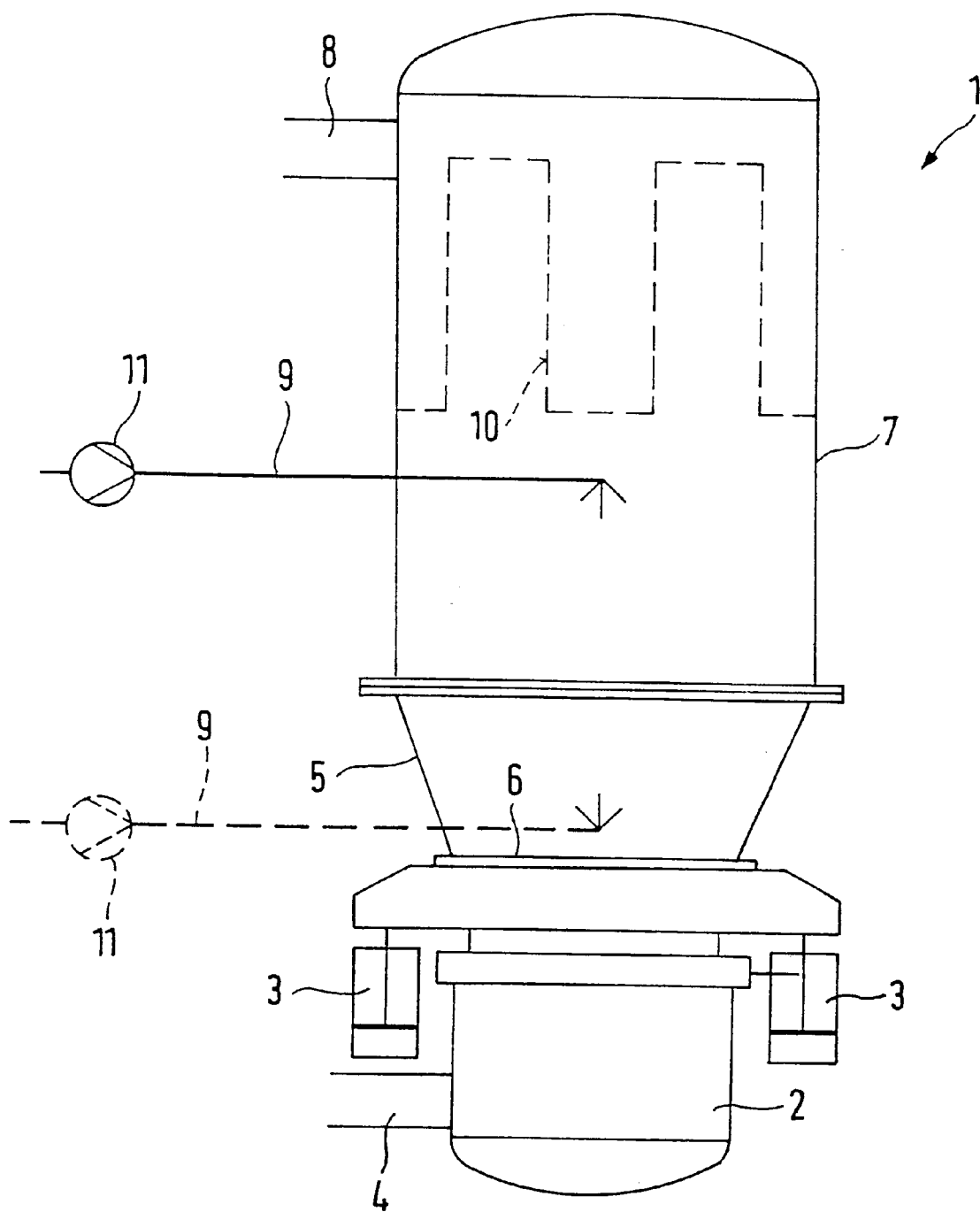

FIG. 2 shows one possible embodiment of a fluidised bed plant for producing the granules.

1 Fluidised bed plant
2 Lower part
3 Pressure device (for example hydraulic cylinder)
4 Feed air channel
5 Material container
6 Inflow base (gas distributor)
7 Filter housing (release zone)
8 Waste air channel
9 Spraying channel with spraying nozzle (top spray and bottom spray position)
10 Product restraining filter
11 Spraying pump Product, powder or granules, is fluidised in a fluidised bed plant 1 by means of a fluidisation gas. The fluidisation gas is thus passed through the fluidised bed plant 1 from the bottom to the top, for example by means of a ventilator not shown. The aim of the fluidisation gas is thus fluidisation of the goods to be treated, convective heat supply to the product or to a spray mist and transporting away of the evaporated quantity of liquid during drying. The fluidisation gas enters via the feed air channel 4 introduced in the lower part 2. Uniform gas distribution over the cross-section of the reaction chamber takes place via an inflow base 6, which at the same time separates the material container 5 from the lower part 2. Technical auxiliaries (for example product restraining filter) to restrain fine-grain product are introduced in the filter housing 7 in the upper region and ensure that product discharge cannot take place in the waste air channel 8 likewise introduced in the upper region of the fluidised bed plant. Liquid product (solution or suspension may be sprayed, via a spraying channel having spraying nozzle 9 and by means of a spraying pump 11 from a vessel not shown, into the fluidised bed plant 1 either from the top (top spray position, shown by continuous line) or from the bottom (bottom spray position, shown by a dashed line). The spray cone thus produced either meets product already placed in the material container 5 and dries there on the particle surface resulting therefrom, or is dried directly in the reaction chamber analogously to the spray-drying conditions and thus forms powder or finely divided granules. Drying which is gentle to the product may be maintained as a result of measuring the product temperature during the fluidised bed process and process control based thereon. The temperature of the fluidisation gas is thus of course selected according to the goods to be treated, and may lie, for example in a range from 15 to 100° C. The resulting product temperature is lower and may preferably be kept lower than 50° C. or better lower than 37° C. during drying or spray granulation.

What is claimed is:

1. A fibrin tissue adhesive formulation containing a mixture of thrombin, and fibrinogen with factor XIII in pourable solid granules, said mixture prepared by:
   (a) providing solutions or suspensions of the thrombin, and the fibrinogen with factor XIII;
   (b) drying the solutions in a fluidised bed apparatus; and
   (c) forming the pourable solid granules with a particle size of 20–1000 μm.

2. The fibrin tissue adhesive formulation of claim 1, wherein the mixture consists of separately dried thrombin and fibrinogen granules.

3. The fibrin tissue adhesive formulation of claim 1, wherein the thrombin and/or fibrinogen granules have a core as carrier.

4. The fibrin tissue adhesive formulation of claim 3, wherein the carrier is selected from water-soluble sugars, sugar substitutes, biological transport substances, or mixtures thereof.

5. A fibrin tissue adhesive formulation containing a mixture of thrombin, and fibrinogen with factor XIII in pourable solid granules, said mixture prepared by:
   (a) providing solutions or suspensions of the thrombin, and the fibrinogen with factor XIII;
   (b) drying the solutions in a fluidised bed apparatus; and
   (c) forming the pourable solid granules with a particle size of 20–1000 μm;
   wherein the granules are mixed granules incorporating the fibrinogen in an inner core and the thrombin in an outer layer thereon.

6. A fibrin tissue adhesive formulation containing a mixture of thrombin, and fibrinogen with factor XIII in pourable solid granules, said mixture prepared by:
   (a) providing solutions or suspensions of the thrombin, and the fibrinogen with factor XIII;
   (b) drying the solutions in a fluidised bed apparatus; and
   (c) forming the pourable solid granules with a particle size of 20–1000 μm; wherein the mixed granules comprise a carrier core, a fibrinogen layer on the core and an outer thrombin layer.

7. The fibrin tissue adhesive formulation of claim 5 or 6, wherein a barrier layer is present between the fibrinogen layer and the outer thrombin layer.

8. The fibrin tissue adhesive formulation of claim 7, wherein the barrier layer is produced by drying solutions of low-molecular polyvinylpyrrolidone; cellulose derivatives; or carbohydrates.

9. The fibrin tissue adhesive formulation of claim 1, wherein the ratio of thrombin to fibrinogen with factor XIII is 1:10 to 1:1000.

10. The fibrin tissue adhesive formulation of claim 9, wherein the ratio of thrombin to fibrinogen with factor XIII is 1:50 to 1:200.

11. The fibrin tissue adhesive formulation of claim 1, wherein the grain diameter of the granules is 30–500 μm.

12. The fibrin tissue adhesive formulation of claim 11, wherein the grain diameter of the granules is 40–200 μm.

13. The fibrin tissue adhesive formulation of claim 1, wherein the granules are provided with an outer barrier layer.

14. The fibrin tissue adhesive formulation of claim 1, wherein thrombin and fibrinogen are produced recombinantly by genetic engineering or biotechnological processes.

15. The fibrin tissue adhesive formulation of claim 1, wherein the solution or suspension contains a calcium salt.

16. A process for producing a fibrin tissue adhesive formulation containing a mixture of thrombin, and fibrinogen with factor XIII in pourable solid granules, which comprises
   (a) providing solutions or suspensions of the thrombin, and the fibrinogen with factor XIII;
   (b) drying the solutions in a fluidised bed apparatus; and
   (c) forming the pourable solid granules at a product temperature not exceeding 50° C., said granules having a particle size of 20–1000 μm.

17. The process of claim 16, wherein:
   (a) a fibrinogen concentrate with factor XIII is sprayed into the fluidised bed apparatus from aqueous solution, dried and isolated;
   (b) a thrombin concentrate is sprayed into the fluidised bed apparatus from aqueous solution, dried and isolated; and
   (c) the granules of fibrinogen and thrombin thus produced are mixed.

18. The process for producing a fibrin tissue adhesive formulation of claim 16, wherein:
   (a) fibrinogen concentrate is sprayed into the fluidised bed apparatus from aqueous solution and dried; and
   (b) thrombin is sprayed onto the dried granules from an organic suspension.

19. The process for producing a fibrin tissue adhesive formulation of claim 16, wherein the solutions or suspensions are sprayed onto a carrier material.

* * * * *

UNITED STATES PATENT AND TRADEMARK OFFICE
Certificate

Patent No. 6,596,318 B2

Patented: July 22, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Armin Prasch, Freiburg (DE); Bernhard Luy, Sulzburg (DE); and Mirna Rapp, Marburg (DE).

Signed and Sealed this Tenth Day of February 2009.

MICHAEL G. WITYSHYN
*Supervisory Patent Examiner*
Art Unit 1651